United States Patent
Krizman

(10) Patent No.: US 9,765,380 B2
(45) Date of Patent: Sep. 19, 2017

(54) TRUNCATED HER2 SRM/MRM ASSAY

(75) Inventor: David Krizman, Gaithersburg, MD (US)

(73) Assignee: Expression Pathology, Inc., Rockville, MD (US)

( * ) Notice: Subject to any disclaimer, the term of this patent is extended or adjusted under 35 U.S.C. 154(b) by 284 days.

(21) Appl. No.: 13/993,045

(22) PCT Filed: Dec. 8, 2011

(86) PCT No.: PCT/US2011/064045
§ 371 (c)(1),
(2), (4) Date: Jul. 19, 2013

(87) PCT Pub. No.: WO2012/078934
PCT Pub. Date: Jun. 14, 2012

(65) Prior Publication Data
US 2013/0302328 A1  Nov. 14, 2013

Related U.S. Application Data

(60) Provisional application No. 61/421,206, filed on Dec. 8, 2010.

(51) Int. Cl.
G01N 33/74 (2006.01)
G01N 30/72 (2006.01)
G01N 33/48 (2006.01)
C12Q 1/37 (2006.01)
G01N 33/68 (2006.01)
C07K 14/71 (2006.01)

(52) U.S. Cl.
CPC ............ C12Q 1/37 (2013.01); C07K 14/71 (2013.01); G01N 33/6848 (2013.01); G01N 33/74 (2013.01); *G01N 30/72* (2013.01); *G01N 30/7233* (2013.01); *G01N 2333/71* (2013.01)

(58) Field of Classification Search
None
See application file for complete search history.

(56) References Cited

U.S. PATENT DOCUMENTS

| | | |
|---|---|---|
| 2003/0059863 A1 | 3/2003 | Clinton et al. |
| 2004/0121946 A9 | 6/2004 | Fikes et al. |
| 2006/0094649 A1 | 5/2006 | Keogh et al. |
| 2009/0136971 A1 | 5/2009 | Krizman et al. |
| 2009/0197852 A9 | 8/2009 | Johnson, Jr. et al. |
| 2009/0253156 A1 | 10/2009 | Patton et al. |
| 2010/0021881 A1 | 1/2010 | Logtenberg et al. |
| 2010/0299081 A1 | 11/2010 | Ashman et al. |
| 2013/0122516 A1 * | 5/2013 | Hong .................. G01N 27/62 435/7.1 |

FOREIGN PATENT DOCUMENTS

| | | | | |
|---|---|---|---|---|
| GB | WO 03087831 A2 * | 10/2003 | ....... | G01N 33/57415 |
| WO | WO 2008/097229 | 8/2008 | | |
| WO | WO 2011140464 A2 * | 11/2011 | ......... | G01N 33/6842 |

OTHER PUBLICATIONS

Huang et al., Clin. Immunol., 2004, 111:202-209.*
Adam et al: "Comprehensive proteomic analysis of breast cancer cell membranes reveals unique proteins with potential roles in clinical cancer", JBC Papers in Press, XX, XX, Jan. 1, 2002 (Jan. 1, 2002), pp. 1-60.
Fulvia Troise et al: "A novel ErbB2 epitope targeted by human antitumor immunoagents", FEBS Journal, vol. 278, No. 7, Apr. 1, 2011 (Apr. 1, 2011), pp. 1156-1166.
Chen et al. Proteomic characterization of Her2/neu-overexpressing breast cancer cells Proteomics 2010, 10, 3800-3810 first published online: Oct. 19, 2010. entire document.
International Search Report dated May 25, 2012, issued in the International Application PCT/US2011/064045.

* cited by examiner

*Primary Examiner* — Hong Sang
(74) *Attorney, Agent, or Firm* — Edell, Shaprio & Finnan, LLC.

(57) ABSTRACT

This disclosure provides ten (10) specific peptides, and particular peptide characteristics, from the cell membrane-bound Her2 protein and a diagnostic assay useful for determining the presence and amount of full length and truncated versions of the full-length Her2 protein in cells derived from formalin fixed paraffin embedded tissue.

19 Claims, 1 Drawing Sheet

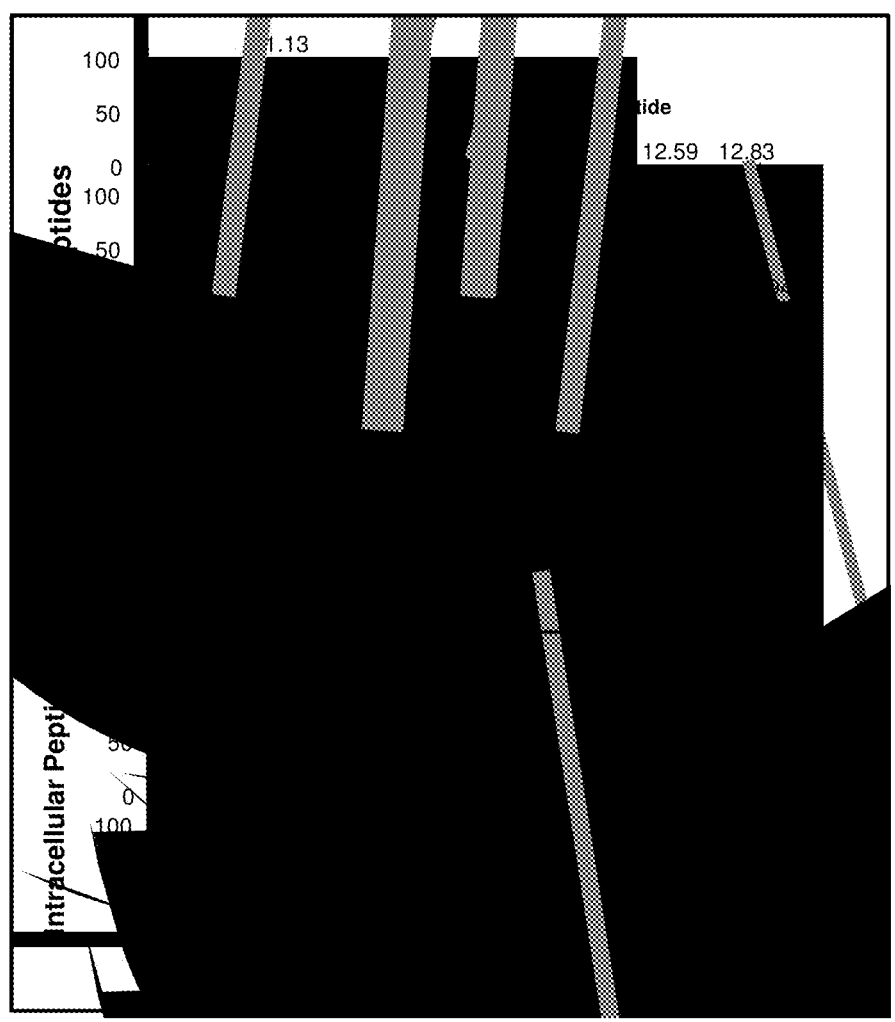

TRUNCATED HER2 SRM/MRM ASSAY

This application is a 371 application of PCT/US2011/064045, filed Dec. 8, 2011, which claims priority to U.S. Provisional Application No. 61/421,206, filed Dec. 8, 2010, the contents of each of which are hereby incorporated by reference in their entireties. This application also contains a sequence listing submitted electronically via EFS-web, which serves as both the paper copy and the computer readable form (CRF) and consists of a file entitled "SeqList-.txt", which was created on Jun. 10, 2013, which is 2,045 bytes in size, and which is also incorporated by reference in its entirety.

INTRODUCTION

Specific peptides derived from subsequences of the full-length Her2 protein (also known as the Neu proto-oncogene, c-ErbB-2, tyrosine kinase-type cell surface receptor HER2, p185erbB2, or CD340), are provided. The peptide sequence and fragmentation/transition ions for each peptide are particularly useful in a mass spectrometry-based Selected Reaction Monitoring (SRM) assay, which can also be referred to as a Multiple Reaction Monitoring (MRM) assay, hereafter referred to as the SRM/MRM assay.

This SRM/MRM assay can be used to detect the presence and quantitatively measure the amount of the full-length Her2 protein and simultaneously detect and quantitatively measure the amount of a truncated version of the full-length Her2 protein in biological samples. This assay is useful for determining whether or not the Her2 protein within cancer cells is full-length or in a truncated form and can be carried out directly in cells procured from cancer patient tissue, as for example formalin fixed cancer tissue. This SRM/MRM assay is very important for individual cancer patients because different therapeutic agents and treatment strategies can be used to treat a particular cancer patient's disease based on; 1) which form of the Her2 protein (full length or truncated) is expressed in their particular cancer, and 2) the absolute and relative amounts of each form (the ratio of full length Her2 to truncated) present in their cancer cells. Thus, optimal treatment decisions can be made about an individual cancer patient based on the knowledge that this SRM/MRM assay provides for that patient's cancer cells.

BRIEF DESCRIPTION OF THE DRAWINGS

FIG. 1 shows results from an SRM/MRM assay performed on a Liquid Tissue® lysate from a cell line that has been formalin fixed and from which a Liquid Tissue lysate has been prepared.

DETAILED DESCRIPTION

Ten (10) specific peptides are provided from the cell membrane-bound Her2 protein and the particular characteristics of the peptides are described. Also provided is a diagnostic assay useful for determining the presence and amount (as compared to the amount of full-length Her2) of truncated versions of the full-length Her2 protein in cells derived from formalin fixed paraffin embedded (FFPE) tissue. Multiple peptides are derived from the intracellular domain of the full-length Her2 protein (ICD) while other multiple peptides are derived from the extracellular domain (ECD) of the full-length Her2 protein. The peptides are shown in Table 1.

TABLE 1

| SEQ ID: | Peptide Sequence | Location |
|---|---|---|
| SEQ ID NO: 1 | SLTEILK | Extracellular Domain |
| SEQ ID NO: 2 | GGVLIQR | Extracellular Domain |
| SEQ ID NO: 3 | VLQGLPR | Extracellular Domain |
| SEQ ID NO: 4 | LPASPETHLDMLR | Extracellular Domain |
| SEQ ID NO: 5 | NNQLALTLIDTNR | Extracellular Domain |
| SEQ ID NO: 6 | GIWIPDGENVK | Intracellular Domain |
| SEQ ID NO: 7 | ELVSEFSR | Intracellular Domain |
| SEQ ID NO: 8 | FVVIQNEDLGPASPLDSTFYR | Intracellular Domain |
| SEQ ID NO: 9 | SGGGDLTLGLEPSEEEAPR | Intracellular Domain |
| SEQ ID NO: 10 | GLQSLPTHDPSPLQR | Intracellular Domain |

These peptides have advantageously been determined to be optimized for analysis of proteins by mass spectrometry and for use in an SRM/MRM mass spectrometry-based assay. More specifically, this SRM/MRM assay can measure any combination of one or more, two or more, three or more, four or more, five or more, six or more, seven or more, eight or more, or nine or more, of these peptides directly in complex protein lysate samples prepared from cells procured from patient tissue samples, such as formalin fixed cancer patient tissue. In one embodiment, at least one intracellular and one extracellular peptide is measured. In another embodiment, any combination of one or more, two or more, three or more, or four or more, intracellular and one or more, two or more, three or more, or four or more extracellular peptides are measure. By measuring at least one or more intracellular and one or more extracellular peptides the amount or ratio of various form of the Her2 receptor can be determined.

Methods of preparing protein samples from formalin-fixed tissue are described in U.S. Pat. No. 7,473,532, the contents of which are hereby incorporated by references in their entirety. The methods described in U.S. Pat. No. 7,473,532 may conveniently be carried out using Liquid Tissue® agents and protocol available from Expression Pathology Inc. (Rockville, Md.).

In principle, any predicted peptide derived from Her2 protein, prepared for example by digesting with a protease of known specificity (e.g. trypsin), can be used as a surrogate reporter to determine the abundance of Her2 protein in a sample using a mass spectrometry-based SRM/MRM assay. Similarly, any predicted peptide sequence containing an amino acid residue at a site that is known to be potentially modified in Her2 protein also might potentially be used to assay the extent of modification of Her2 protein in a sample. Surprisingly, however, it has been found that many of the very large number of potential peptide sequences from the Her2 protein are unsuitable or ineffective for use in mass spectrometry-based SRM/MRM assays. The peptides are, for example, difficult to detect by mass spectrometry, or are unstable under the conditions used to obtain the peptides from the parent protein. This is especially found to be the case when interrogating protein lysates prepared from formalin fixed tissue using the liquid tissue protocol provided in U.S. Pat. No. 7,473,532. The liquid tissue protocol and reagents are able to prepare peptides from formalin fixed, paraffin embedded tissue for mass spectrometry analysis by performing the following experimental steps to the tissue. First, the tissue is placed into a tube containing a buffer where the tissue is heated in the buffer for an extended period of time at elevated temperatures. The buffer is a neutral buffer, a Tris-based buffer, or a buffer containing a detergent, and advantageously is a buffer that does not interfere with mass spectrometric analysis. Next, the tissue is treated with one or more proteases including, but not limited to, trypsin, chymotrypsin, and or pepsin. Unexpectedly it was found to be necessary to experimentally identify candidate modified and unmodified peptides in actual liquid tissue lysates in order to develop a reliable and accurate SRM/MRM assay for the Her2 protein. In particular it was found that many tryptic peptides from the Her2 protein could not be detected efficiently or at all in a liquid tissue lysate from formalin fixed, paraffin embedded tissue. Accordingly, those peptides from the Her2 protein that can be detected in a liquid tissue lysate prepared from a formalin fixed tissue sample are the peptides for which SRM/MRM assays can be developed to determine full length or truncated versions of the Her2 protein in a biological sample.

The most widely and advantageously available form of tissues from cancer patients tissue is formalin fixed, paraffin embedded tissue. Formaldehyde/formalin fixation of surgically removed tissue is by far and away the most common method of preserving cancer tissue samples worldwide and is the accepted convention in standard pathology practice. Aqueous solutions of formaldehyde are referred to as formalin. "100%" formalin consists of a saturated solution of formaldehyde (this is about 40% by volume or 37% by mass) in water, with a small amount of stabilizer, usually methanol, to limit oxidation and degree of polymerization. The most common way in which tissue is preserved is to soak whole tissue for extended periods of time (8 hours to 48 hours) in aqueous formaldehyde, commonly termed 10% neutral buffered formalin, followed by embedding the fixed whole tissue in paraffin wax for long term storage at room temperature. Thus molecular analytical methods to analyze formalin fixed cancer tissue will be the most accepted and heavily utilized methods for analysis of cancer patient tissue.

Results from the SRM/MRM assay can be used to correlate accurate and precise quantitative levels of both the full-length Her2 protein and the presence of truncated forms of the full-length Her2 protein within the specific cancer of the patient from whom the tissue was collected and preserved. This not only provides diagnostic information about the cancer, but also permits a physician or other medical professional to determine appropriate therapy for the patient. Such an assay that provides diagnostically and therapeutically important information about levels of protein expression in a diseased tissue or other patient sample is termed a companion diagnostic assay. For example, such an assay can be designed to diagnose the stage or degree of a cancer and determine a therapeutic agent to which a patient is most likely to respond. Identifying specific forms of truncated Her2 protein is not important to this assay. The fact that truncation of Her2 is responsible for resistance to drugs that inhibit Her2 protein activity, and the ability to detect and quantify the degree of truncation allows an accurate prediction of whether or not a cancer may be resistant to Her2 antagonists.

The methods described herein can be performed by the method of Selected Reaction Monitoring mass spectrometry. In this method, detection of two or more peptides from the list in Table 1, where peptides identify both the ICD and ECD in a MRM/SRM analysis of a liquid tissue lysate prepared from FFPE tissue, indicates presence of the full-length Her2 protein in the cells procured from FFPE tissue. Conversely; absence of one or more peptides from the list in Table 1 that specifically derive from the ECD, with simultaneous detection of the one or more peptides from the ICD, indicates that the Her2 protein is present in a truncated form. Additionally, a reduction in the quantitative amount of the peptide MRM/SRM signal of the ECD peptide(s) as compared to the MRM/SRM signal of the ICD peptide(s) (the ratio) indicates at least the presence of a truncated version or versions of the Her2 protein and the ratio of the ECD peptide signals to the ICD peptide signals indicates the ratio of the truncated Her2 protein to the full-length Her2 protein. The methods are performed directly on cancer cells obtained from the patient's cancer tissue, most preferably by the method of tissue microdissection, and are important for cancer treatment because different therapeutic reagents interact with and inactivate the full length and truncated forms of the Her2 protein, respectively. Accordingly, by determining whether the Her2 protein is present in a full length form and/or in a truncated form in a patient's cancer cells allows the selection of one or more appropriate therapeutic agents to administer to the patient in order to kill the cancer cells remaining in the patient.

Detection of peptides and determining quantitative levels of these Her2 peptides are determined mass spectrometrically by the SRM/MRM methodology, whereby the SRM/MRM signature chromatographic peak area of each peptide is determined within a complex peptide mixture present in a liquid tissue lysate. Quantitative levels of the Her2 protein are then determined by the SRM/MRM methodology whereby the SRM/MRM signature chromatographic peak area of each of the individual peptides from the Her2 protein in one biological sample is compared to the SRM/MRM signature chromatographic peak area of a known amount of a "spiked" internal standard for each of the individual peptides. In one embodiment, the internal standard is a synthetic version of the same exact Her2 peptide that contains one or more amino acid residues labeled with one or more heavy isotopes. Such isotope labeled internal standards are synthesized so that mass spectrometry analysis generates a predictable and consistent SRM/MRM signature chromatographic peak that is different and distinct from the native Her2 peptide chromatographic signature peak and which can be used as a comparator peak. Thus when the internal standard is spiked in known amounts into a protein or peptide preparation from a biological sample and analyzed by mass spectrometry, the SRM/MRM signature chromatographic peak area of the native peptide is compared to the SRM/MRM signature chromatographic peak area of the internal standard peptide, and this numerical comparison indicates either the absolute molarity and/or absolute weight of the native peptide present in the original protein preparation from the biological sample. Quantitative data for fragment peptides are displayed according to the amount of protein analyzed per sample.

In order to develop the SRM/MRM assay for each peptide derived from the Her2 protein additional information beyond simply the peptide sequence needs to be utilized by the mass spectrometer. That additional information is important in directing and instructing the mass spectrometer, (e.g., a triple quadrupole mass spectrometer) to perform the correct and focused analysis of a specific targeted peptide. An important consideration when conducting an SRM/MRM assay is that such an assay may be effectively performed on a triple quadrupole mass spectrometer. That type of a mass spectrometer may be considered to be the most suitable instrument for analyzing a single isolated target peptide within a very complex protein lysate that may consist of hundreds of thousands to millions of individual peptides from all the proteins contained within a cell. The additional information provides the triple quadrupole mass spectrometer with the correct directives to allow analysis of a single isolated target peptide within a very complex protein lysate that may consist of hundreds of thousands to millions of individual peptides from all the proteins contained within a cell. Although SRM/MRM assays can be developed and performed on any type of mass spectrometer, including a MALDI, ion trap, or triple quadrupole, presently the most advantageous instrument platform for SRM/MRM assay is often considered to be a triple quadrupole instrument platform. The additional information about target peptides in general, and about three (3) specific Her2 peptides, may include one or more of the mono isotopic mass of each peptide, its precursor charge state, the precursor m/z value, the m/z transition ions, and the ion type of each transition ion. The necessary additional information as described for the ten (10) Her2 peptides is shown by example in Table 2 but is also necessary for the other peptides contained in Table 1, and this information is implied for each of the other peptides listed in Table 1 by way of example from the three (3) peptides in Table 2.

Certain Embodiments

1. A method for detecting the presence and measuring the level of the Her2 protein and the degree of truncated versions of the Her2 protein in a protein digest prepared from a biological sample, comprising detecting specific peptides from the Her2 protein in a protein digest prepared from said biological sample using mass spectrometry; and calculating the level of these 2 versions of the Her2 protein in said sample wherein said level is an absolute level of both versions of the Her2 protein.

2. The method of embodiment 1, further comprising the step of fractionating said protein digest prior to detecting said peptides.

3. The method of embodiment 2, wherein said fractionating step is selected from the group consisting of gel electrophoresis, liquid chromatography, capillary electrophoresis, nano-reversed phase liquid chromatography, high performance liquid chromatography, or reverse phase high performance liquid chromatography.

4. The method of embodiment 1, wherein said protein digest of said biological sample is prepared by the liquid tissue protocol.

5. The method of embodiment 1, wherein said protein digest comprises a protease digest.

6. The method of embodiment 5, wherein said protein digest comprises a trypsin digest.

7. The method of embodiment 1, wherein mass spectrometry comprises tandem mass spectrometry, ion trap mass spectrometry, triple quadrupole mass spectrometry, MALDI-TOF mass spectrometry, MALDI mass spectrometry, and/or time of flight mass spectrometry.

TABLE 2

| SEQ ID | Peptide Sequence | Mono Isotopic Mass | Precursor Charge State | Precursor m/z | TransitionIon m/z | Type |
|---|---|---|---|---|---|---|
| SEQ ID NO: 9 | SGGGDLTLGLEPSEEEAPR | 1912.901 | 2 | 957.458 | 914.421 | y8 |
| | | | 2 | 957.458 | 1043.464 | y9 |
| | | | 2 | 957.458 | 1213.569 | y11 |
| SEQ ID NO: 4 | LPASPETHLDMLR | 1478.755 | 3 | 493.925 | 534.27 | y4 |
| | | | 3 | 493.925 | 556.282 | y9 |
| | | | 3 | 493.925 | 635.316 | y11 |
| | | | 3 | 493.925 | 647.354 | y5 |
| | | | 3 | 493.925 | 784.413 | y6 |
| SEQ ID NO: 5 | NNQLALTLIDTNR | 1484.795 | 2 | 743.404 | 832.452 | y7 |
| | | | 2 | 743.404 | 945.536 | 78 |
| | | | 2 | 743.404 | 1016.573 | y9 |

FIG. 1 shows results from an SRM/MRM assay performed on a liquid tissue lysate from a cell line that has been formalin fixed and from which a liquid tissue lysate has been prepared. Results show the ability to detect and quantitate two (2) peptides from the extracellular domain of the full-length Her2 protein and to detect and quantitate one (1) peptide from the intracellular domain of the full-length Her2 protein. Data from the assay indicate the presence of the unique SRM/MRM signature chromatographic peaks for both the internal standard and the endogenous peptides for each of the three (3) peptides in the liquid tissue sample prepared from the formalin fixed cell line. This SRM/MRM assay was developed for quantitation of the Her2 protein, and determination of the presence of truncated versions of the Her2 protein, on a triplequadrupole mass spectrometer using the information specified in Tables 1 and 2.

8. The method of embodiment 7, wherein the mode of mass spectrometry used is Selected Reaction Monitoring (SRM), Multiple Reaction Monitoring (MRM), and/or multiple Selected Reaction Monitoring (mSRM).

9. The method of embodiments 1 and 8, wherein the Her2 fragment peptides comprise the amino acid sequences as set forth as SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

10. The method of embodiment 1, wherein the biological sample is a blood sample, a urine sample, a serum sample, an ascites sample, a saliva sample, a cell, or a solid tissue.

11. The method of embodiment 10, wherein the tissue is formalin fixed tissue.

12. The method of embodiment 10, wherein the tissue is paraffin embedded tissue.

13. The method of embodiment 10, wherein the tissue is obtained from a tumor.

14. The method of embodiment 13, wherein the tumor is a primary tumor.

15. The method of embodiment 13, wherein the tumor is a secondary tumor.

16. The method of embodiment 1, further comprising detecting and quantifying all 10 (10) Her2 fragment peptides.

17. The method of embodiment 16, wherein quantifying the ten (10) Her2 fragment peptides comprises comparing an amount of each Her2 fragment peptide corresponding to an amino acid sequence of about 8 to about 45 amino acid residues of Her2 as shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10 in one biological sample to the amount of the same Her2 fragment peptide in a different and separate biological sample.

18. The method of embodiment 16, wherein quantifying the Her2 fragment peptide comprises determining the amount of one or more of the ten (10) Her2 fragment peptides in a biological sample by comparing to a spiked internal standard peptide of known amount, wherein both the native peptide in the biological sample and the internal standard peptide corresponds to the same amino acid sequence of about 8 to about 45 amino acid residues of Her2 as shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

19. The method of embodiment 18, wherein the internal standard peptide is an isotopically labeled peptide.

20. The method of embodiment 19, wherein the isotopically labeled internal standard peptide comprises one or more heavy stable isotopes selected from $^{18}O$, $^{17}O$, $^{34}S$, $^{15}N$, $^{13}C$, $^{2}H$ or combinations thereof.

21. The method of embodiment 1, further comprising obtaining the biological sample from a subject, wherein detecting and quantifying one or more of the ten (10) unmodified Her2 fragment peptides in the protein digest indicates the presence of the full-length Her2 protein, presence of truncated version or versions of the full length Her2 protein, and/or combination of the presence of both and an association with cancer in the subject.

22. The method of embodiment 21, further comprising correlating a detected and quantitated amount of the Her2 fragment peptide to the diagnostic stage/grade/status of the cancer.

23. The method of any one of embodiments 16-22, further comprising selecting a treatment for the subject based on the presence, absence, or quantified levels of one or more of the ten (10) Her2 fragment peptides in the protein digest.

24. The method any one of embodiments 16-23, further comprising administering a therapeutically effective amount of a therapeutic agent targeted specifically to the Her2 protein, wherein the treatment decision about which agent and amount of agent used for treatment is based upon specific levels of the full-length Her2 protein or truncated versions of the Her2 protein in the biological sample.

25. The method of embodiments 23 and 24, wherein therapeutic agents include those designed to specifically bind and inhibit either the full-length Her2 protein or truncated versions of the Her2 protein and its biological activity, and include for example but are not limited to the drugs herceptin, trastuzumab, and lapatinib.

26. The method of embodiments 24 and 25, wherein detecting and quantitating the full-length or truncated versions of the full-length Her2 protein can be combined with detecting and quantitating other peptides from other proteins in multiplex so that the treatment decision about which agent and amount of agent used for treatment is based upon specific levels of the Her2 fragment peptide in combination with other peptides/proteins in the biological sample.

27. The method of embodiments 10 and 21, wherein the biological sample is formalin fixed tumor tissue that has been processed for quantitative analysis of the modified or unmodified Her2 fragment peptides by the liquid tissue protocol and reagents.

28. A composition comprising two or more, three or more, four or more, five or more, six or more, seven or more, eight or more, or nine or more, isolated peptides of SEQ ID NOs. 1-10.

29. A composition comprising:
(i) one or more, two or more, three or more, or four or more, Her2 intracellular peptides; and
(ii) one or more, two or more, three or more, or four or more Her2 extracellular peptides, wherein said intracellular and extracellular peptides are selected from peptides having the sequence of SEQ ID Nos. 1-10.

30. The composition of embodiments 28 or 29 wherein said composition is free or substantially free of other peptides derived from the Her2.

31. The composition of embodiment 30, wherein said peptides are isotopically labeled internal standard peptides that comprises one or more, two or more, or three or more, heavy stable isotopes selected from $^{18}O$, $^{17}O$, $^{34}S$, $^{15}N$, $^{13}C$, $^{2}H$ or combinations thereof.

32. The composition of embodiments 28 or 29, wherein said composition is substantially pure or free of other cellular components selected from any combination of other proteins, membranes lipids and nucleic acids.

33. The composition of embodiment 32, wherein said peptides are isotopically labeled internal standard peptides that comprises one or more, two or more, or three or more, heavy stable isotopes selected from $^{18}O$, $^{17}O$, $^{34}S$, $^{15}N$, $^{13}C$, $^{2}H$ or combinations thereof.

The above description and exemplary embodiments of methods and compositions are illustrative of the scope of the present disclosure. Because of variations which will be apparent to those skilled in the art, however, the present disclosure is not intended to be limited to the particular embodiments described above.

The invention claimed is:

1. A method for detecting the presence and measuring the level of full length Her2 protein and truncated Her2 protein in a human biological sample of formalin-fixed tissue, comprising detecting and quantifying the amount of a Her2 fragment peptide in a protein digest prepared from said human biological sample using mass spectrometry; and calculating the level of full length and truncated Her2 protein in said sample wherein said level is an absolute level, wherein said Her2 fragment peptide is SEQ ID NO:7.

2. The method of claim 1, further comprising the step of fractionating said protein digest prior to detecting said Her2 fragment peptide.

3. The method of claim 2, wherein said fractionating step is selected from the group consisting of liquid chromatography, nano-reversed phase liquid chromatography, high performance liquid chromatography, and reversed phase high performance liquid chromatography.

4. The method of claim 1, wherein said protein digest comprises a protease digest.

5. The method of claim 4, wherein said protein digest comprises a trypsin digest.

6. The method of claim 1, wherein said mass spectrometry comprises tandem mass spectrometry, ion trap mass spectrometry, triple quadrupole mass spectrometry, MALDI-TOF mass spectrometry, MALDI mass spectrometry, and/or time of flight mass spectrometry.

7. The method of claim 1, wherein the tissue is paraffin embedded tissue.

8. The method of claim 1, wherein the tissue is obtained from a tumor.

9. The method of claim 8, wherein the tumor is a primary tumor.

10. The method of claim 8, wherein the tumor is a secondary tumor.

11. The method of claim 1, wherein quantifying the amount of said Her2 fragment peptide comprises comparing the amount of said Her2 fragment peptide in a protein digest of one biological sample to the amount of the same Her2 fragment peptide in a protein digest of a different and separate biological sample.

12. The method of claim 1, wherein quantifying the amount of said Her2 fragment peptide comprises determining the amount of said Her2 fragment peptide in a protein digest of a biological sample by comparing to a spiked internal standard peptide of known amount, wherein both the peptide in the biological sample and the internal standard peptide have the same respective amino acid sequences and wherein the internal standard peptide is an isotopically labeled peptide.

13. The method of claim 12, wherein said isotopically labeled internal standard peptide comprises one or more heavy stable isotopes selected from $^{18}O$, $^{17}O$, $^{34}S$, $^{15}N$, $^{13}C$, $^{2}H$ or combinations thereof.

14. The method of claim 1, further comprising obtaining the biological sample from a subject, wherein detecting and quantifying the amount of said Her2 fragment peptide in the protein digest indicates the presence of the full-length and truncated Her2 protein and an association with cancer in the subject.

15. The method of claim 14, further comprising correlating the amount of the full length and truncated Her2 protein to the diagnostic stage/grade/status of the cancer.

16. The method of claim 1, further comprising selecting a treatment for the subject from whom the biological sample was obtained based on the amount of full length and truncated Her2 protein in the protein digest.

17. The method of claim 16, further comprising administering a therapeutically effective amount of a therapeutic agent targeted specifically to the Her2 protein to said subject.

18. The method of claim 17, wherein said therapeutic agent is selected from the group consisting of trastuzumab and lapatinib.

19. The method of claim 17, wherein measuring the level of full-length and truncated Her2 protein is combined with detecting and quantitating other peptides from other proteins in a multiplex format so that the agent and amount of the agent used for treatment is selected based upon specific levels of truncated and full length Her2 fragment in combination with other peptides from other proteins in the biological sample.

\* \* \* \* \*

SEQUENCE LISTING

```
<160> NUMBER OF SEQ ID NOS: 10

<210> SEQ ID NO 1
<211> LENGTH: 7
<212> TYPE: PRT
<213> ORGANISM: Homo sapiens
```

```
<400> SEQUENCE: 1

Ser Leu Thr Glu Ile Leu Lys
1               5

<210> SEQ ID NO 2
<211> LENGTH: 7
<212> TYPE: PRT
<213> ORGANISM: Homo sapiens

<400> SEQUENCE: 2

Gly Gly Val Leu Ile Gln Arg
1               5

<210> SEQ ID NO 3
<211> LENGTH: 7
<212> TYPE: PRT
<213> ORGANISM: Homo sapiens

<400> SEQUENCE: 3

Val Leu Gln Gly Leu Pro Arg
1               5

<210> SEQ ID NO 4
<211> LENGTH: 13
<212> TYPE: PRT
<213> ORGANISM: Homo sapiens

<400> SEQUENCE: 4

Leu Pro Ala Ser Pro Glu Thr His Leu Asp Met Leu Arg
1               5                   10

<210> SEQ ID NO 5
<211> LENGTH: 13
<212> TYPE: PRT
<213> ORGANISM: Homo sapiens

<400> SEQUENCE: 5

Asn Asn Gln Leu Ala Leu Thr Leu Ile Asp Thr Asn Arg
1               5                   10

<210> SEQ ID NO 6
<211> LENGTH: 11
<212> TYPE: PRT
<213> ORGANISM: Homo sapiens

<400> SEQUENCE: 6

Gly Ile Trp Ile Pro Asp Gly Glu Asn Val Lys
1               5                   10

<210> SEQ ID NO 7
<211> LENGTH: 8
<212> TYPE: PRT
<213> ORGANISM: Homo sapiens

<400> SEQUENCE: 7

Glu Leu Val Ser Glu Phe Ser Arg
1               5

<210> SEQ ID NO 8
<211> LENGTH: 21
<212> TYPE: PRT
<213> ORGANISM: Homo sapiens

<400> SEQUENCE: 8
```

-continued

```
Phe Val Val Ile Gln Asn Glu Asp Leu Gly Pro Ala Ser Pro Leu Asp
1               5                   10                  15

Ser Thr Phe Tyr Arg
            20

<210> SEQ ID NO 9
<211> LENGTH: 19
<212> TYPE: PRT
<213> ORGANISM: Homo sapiens

<400> SEQUENCE: 9

Ser Gly Gly Gly Asp Leu Thr Leu Gly Leu Glu Pro Ser Glu Glu Glu
1               5                   10                  15

Ala Pro Arg

<210> SEQ ID NO 10
<211> LENGTH: 15
<212> TYPE: PRT
<213> ORGANISM: Homo sapiens

<400> SEQUENCE: 10

Gly Leu Gln Ser Leu Pro Thr His Asp Pro Ser Pro Leu Gln Arg
1               5                   10                  15
```